United States Patent
Bhadri et al.

(10) Patent No.: US 10,219,695 B2
(45) Date of Patent: Mar. 5, 2019

(54) ENHANCED VISUALIZATION ILLUMINATION SYSTEM

(71) Applicant: Doheny Eye Institute, Los Angeles, CA (US)

(72) Inventors: Prashant Bhadri, Los Angeles, CA (US); James Lescoulie, Irvine, CA (US); Sophia Fang, Los Angeles, CA (US); Matthew McCormick, Yucaipa, CA (US); Ralph Kerns, Laguna Niguel, CA (US); Mark Humayun, Glendale, CA (US); Aaron Barnes, Washington, DC (US)

(73) Assignee: DOHENY EYE INSTITUTE, Los Angeles, CA (US)

( * ) Notice: Subject to any disclaimer, the term of this patent is extended or adjusted under 35 U.S.C. 154(b) by 0 days.

(21) Appl. No.: 15/680,899

(22) Filed: Aug. 18, 2017

(65) Prior Publication Data

US 2017/0347883 A1 Dec. 7, 2017

Related U.S. Application Data

(60) Continuation of application No. 13/190,142, filed on Jul. 25, 2011, now abandoned, which is a division of
(Continued)

(51) Int. Cl.
*A61B 3/13* (2006.01)
(52) U.S. Cl.
CPC .................................... *A61B 3/13* (2013.01)
(58) Field of Classification Search
CPC ................................ A61B 3/0008; A61B 3/13
See application file for complete search history.

(56) References Cited

U.S. PATENT DOCUMENTS

| 654,390 A | 7/1900 | Fessenden |
| 3,586,424 A * | 6/1971 | Schenk ................... A61B 3/13 351/213 |

(Continued)

FOREIGN PATENT DOCUMENTS

| CN | 1828128 | 9/2006 |
| EP | 1236439 | 9/2002 |

(Continued)

OTHER PUBLICATIONS

Everdell, et al., "Improving Ocular Disease Screening by LED Illumination of the Eye"; Medical News Today; press release available online at http://www.medicalnewstoday.com/articles/199575.php, on Sep. 1, 2010.
(Continued)

*Primary Examiner* — Nicholas Woodall
(74) *Attorney, Agent, or Firm* — Snell & Wilmer LLP (57) ABSTRACT

A first light source producing a first light beam with a first intensity and a second light source producing a second light beam with a second intensity. A light filter device receives the first light beam and transmits a filtered portion of the first light beam. A first angling device reflects the filtered portion of the first light beam in a first angled direction and a second angling device reflects the second light beam in a second angled direction. A mirror receives and in turn reflects the filtered portion of the first light beam reflected by the first angling device and the second light beam reflected by the second angling device to form a converged light beam with a third intensity.

10 Claims, 6 Drawing Sheets

Related U.S. Application Data application No. 12/641,269, filed on Dec. 17, 2009, now abandoned, which is a continuation of application No. 11/938,233, filed on Nov. 9, 2007, now Pat. No. 7,654,716.

(60) Provisional application No. 60/858,176, filed on Nov. 10, 2006.

(56) References Cited

U.S. PATENT DOCUMENTS

| | | | |
|---|---|---|---|
| 3,775,606 A | 11/1973 | Bazell | |
| 3,798,435 A | 3/1974 | Schindl | |
| 3,884,238 A | 5/1975 | O'Malley et al. | |
| 3,930,504 A * | 1/1976 | de Laforcade | A61B 18/20 359/740 |
| 3,990,453 A | 11/1976 | Douvas et al. | |
| 4,019,514 A | 4/1977 | Banko | |
| 4,117,843 A | 10/1978 | Banko | |
| 4,168,707 A | 9/1979 | Douvas et al. | |
| 4,196,460 A | 4/1980 | Schreckendgust | |
| 4,200,106 A | 4/1980 | Dinkelkamp et al. | |
| 4,311,138 A | 1/1982 | Sugarman | |
| 4,324,243 A | 4/1982 | Helfgott et al. | |
| 4,546,761 A | 10/1985 | McCullough | |
| 4,551,129 A | 11/1985 | Coleman et al. | |
| 4,651,257 A | 3/1987 | Gehly | |
| 4,820,264 A | 4/1989 | Matsui et al. | |
| 5,009,487 A | 4/1991 | Reiner | |
| 5,115,124 A | 5/1992 | Muto et al. | |
| 5,147,354 A | 9/1992 | Boutacoff et al. | |
| 5,219,444 A | 6/1993 | Chiaramonte et al. | |
| 5,419,323 A | 5/1995 | Kittrell et al. | |
| 5,421,337 A | 6/1995 | Richards-Kortum et al. | |
| 5,422,792 A | 6/1995 | Neumann | |
| 5,425,730 A | 6/1995 | Luloh | |
| 5,433,702 A | 7/1995 | Zelman et al. | |
| 5,554,097 A | 9/1996 | Guy | |
| 5,562,100 A | 10/1996 | Kittrell et al. | |
| 5,570,698 A | 11/1996 | Liang et al. | |
| 5,586,163 A | 12/1996 | Goldstein | |
| 5,612,540 A | 3/1997 | Richards-Kortum et al. | |
| 5,634,711 A | 6/1997 | Kennedy et al. | |
| 5,697,373 A | 12/1997 | Richards-Kortum et al. | |
| 5,699,795 A | 12/1997 | Richards-Kortum et al. | |
| 5,725,514 A | 3/1998 | Grinblat et al. | |
| 5,733,739 A | 3/1998 | Zakim et al. | |
| 5,818,052 A | 10/1998 | Elabd | |
| 5,842,995 A | 12/1998 | Mahadevan-Jansen et al. | |
| 5,918,973 A | 7/1999 | Nojiri | |
| 5,920,399 A | 7/1999 | Sandison et al. | |
| 5,957,902 A | 9/1999 | Teves | |
| 5,989,262 A | 11/1999 | Josephberg | |
| 5,993,001 A | 11/1999 | Bursell et al. | |
| 6,016,038 A | 1/2000 | Mueller et al. | |
| 6,059,792 A | 5/2000 | Josephberg | |
| 6,069,689 A * | 5/2000 | Zeng | A61B 5/0059 356/301 |
| 6,117,127 A | 9/2000 | Helmreich et al. | |
| 6,135,965 A | 10/2000 | Tumer et al. | |
| 6,150,774 A | 11/2000 | Mueller et al. | |
| 6,158,437 A | 12/2000 | Vagley | |
| 6,160,835 A | 12/2000 | Kwon | |
| 6,166,496 A | 12/2000 | Lys et al. | |
| 6,178,346 B1 | 1/2001 | Amundson et al. | |
| 6,183,086 B1 | 2/2001 | Neubert | |
| 6,206,014 B1 | 3/2001 | Cameron et al. | |
| 6,211,626 B1 | 4/2001 | Lys et al. | |
| 6,230,046 B1 | 5/2001 | Crane et al. | |
| 6,270,491 B1 | 8/2001 | Toth et al. | |
| 6,280,059 B1 | 8/2001 | Ito et al. | |
| 6,292,901 B1 | 9/2001 | Lys et al. | |
| 6,340,868 B1 | 1/2002 | Lys et al. | |
| 6,357,877 B2 | 3/2002 | Takada | |
| D457,667 S | 5/2002 | Piepgras et al. | |
| D457,669 S | 5/2002 | Piepgras et al. | |
| D457,974 S | 5/2002 | Piepgras et al. | |
| D458,395 S | 6/2002 | Piepgras et al. | |
| 6,405,863 B1 | 6/2002 | Dhindsa | |
| 6,425,677 B1 | 7/2002 | Chuang | |
| 6,436,035 B1 | 8/2002 | Toth et al. | |
| D463,610 S | 9/2002 | Piepgras et al. | |
| 6,459,919 B1 | 10/2002 | Lys et al. | |
| D468,035 S | 12/2002 | Blanc et al. | |
| 6,499,863 B2 * | 12/2002 | Dewald | F21V 5/048 348/E5.137 |
| 6,513,962 B1 | 2/2003 | Mayshack et al. | |
| 6,528,954 B1 | 3/2003 | Lys et al. | |
| 6,539,942 B2 | 4/2003 | Schwartz et al. | |
| 6,548,967 B1 | 4/2003 | Dowling et al. | |
| 6,577,080 B2 | 6/2003 | Lys et al. | |
| 6,579,255 B2 | 6/2003 | Kadziauskas et al. | |
| 6,593,101 B2 | 7/2003 | Richards-Kortum et al. | |
| 6,608,453 B2 | 8/2003 | Morgan et al. | |
| 6,623,500 B1 | 9/2003 | Cook et al. | |
| 6,624,597 B2 | 9/2003 | Dowling et al. | |
| 6,639,674 B2 | 10/2003 | Sokolov et al. | |
| 6,652,452 B1 | 11/2003 | Seifert et al. | |
| 6,685,730 B2 | 2/2004 | West et al. | |
| 6,717,376 B2 | 4/2004 | Lys et al. | |
| 6,720,745 B2 | 4/2004 | Lys et al. | |
| D491,678 S | 6/2004 | Piepgras et al. | |
| D492,042 S | 6/2004 | Piepgras et al. | |
| 6,766,184 B2 | 7/2004 | Utzinger et al. | |
| 6,769,546 B2 | 8/2004 | Busch | |
| 6,774,584 B2 | 8/2004 | Lys et al. | |
| 6,777,891 B2 | 8/2004 | Lys et al. | |
| 6,781,329 B2 | 8/2004 | Mueller et al. | |
| 6,786,628 B2 | 9/2004 | Steen et al. | |
| 6,788,011 B2 | 9/2004 | Mueller et al. | |
| 6,824,294 B2 | 11/2004 | Cao | |
| 6,886,964 B2 | 5/2005 | Gardiner et al. | |
| 6,934,576 B2 | 8/2005 | Camacho et al. | |
| 6,963,175 B2 | 11/2005 | Archenhold et al. | |
| 6,964,490 B2 | 11/2005 | Scholz | |
| 6,965,205 B2 | 11/2005 | Piepgras et al. | |
| 6,975,079 B2 | 12/2005 | Lys et al. | |
| 7,014,336 B1 | 3/2006 | Ducharme et al. | |
| 7,020,370 B2 | 3/2006 | Harris | |
| 7,038,398 B1 | 5/2006 | Lys et al. | |
| 7,048,379 B2 | 5/2006 | Miller et al. | |
| 7,063,436 B2 | 6/2006 | Steen et al. | |
| 7,064,498 B2 | 6/2006 | Dowling et al. | |
| 7,116,437 B2 | 10/2006 | Weinstein et al. | |
| 7,130,115 B2 | 10/2006 | Olszak et al. | |
| 7,132,785 B2 | 11/2006 | Ducharme | |
| 7,161,311 B2 | 1/2007 | Mueller et al. | |
| 7,161,313 B2 | 1/2007 | Piepgras et al. | |
| 7,174,094 B2 | 2/2007 | Steinkamp | |
| 7,184,610 B2 | 2/2007 | Weinstein et al. | |
| 7,186,003 B2 | 3/2007 | Dowling et al. | |
| 7,229,202 B2 | 6/2007 | Sander | |
| 7,236,815 B2 | 6/2007 | Richards-Kortum et al. | |
| 7,245,273 B2 | 7/2007 | Eberl et al. | |
| 7,255,457 B2 | 8/2007 | Ducharme et al. | |
| 7,270,439 B2 | 9/2007 | Horrell et al. | |
| 7,284,861 B2 | 10/2007 | Fujieda | |
| 7,308,296 B2 | 12/2007 | Lys et al. | |
| 7,311,401 B2 | 12/2007 | Goldfain et al. | |
| 7,365,844 B2 | 4/2008 | Richards-Kortum et al. | |
| 7,387,405 B2 | 6/2008 | Ducharme et al. | |
| 7,420,153 B2 | 9/2008 | Palmer et al. | |
| 7,422,327 B2 | 9/2008 | Smith | |
| 7,458,375 B2 | 12/2008 | Schwartz et al. | |
| 7,488,088 B2 | 2/2009 | Brukilacchio | |
| 7,488,101 B2 | 2/2009 | Brukilacchio | |
| 7,499,634 B2 | 3/2009 | Yogesan et al. | |
| 7,572,028 B2 | 8/2009 | Mueller et al. | |
| 7,578,391 B2 | 8/2009 | Nakamura | |
| 7,614,763 B2 | 11/2009 | Leibinger et al. | |
| 7,625,098 B2 | 12/2009 | Rains, Jr. et al. | |
| 7,652,772 B2 | 1/2010 | Backman et al. | |
| 7,654,716 B1 | 2/2010 | Bhadri et al. | |
| 7,658,708 B2 | 2/2010 | Schwartz et al. | |

(56) References Cited

U.S. PATENT DOCUMENTS

| | | |
|---|---|---|
| D626,238 S | 3/2010 | Zinnanti |
| 7,677,730 B2 | 3/2010 | Shimizu |
| 7,699,864 B2 | 4/2010 | Kick et al. |
| 7,710,007 B2 | 5/2010 | Liang |
| 7,731,387 B2 | 6/2010 | Cortenraad et al. |
| 7,762,664 B2 | 7/2010 | Fink |
| 7,772,534 B2 | 8/2010 | Ito |
| 7,783,346 B2 | 8/2010 | Smith et al. |
| 7,801,590 B2 | 9/2010 | Feldman et al. |
| 7,845,823 B2 | 12/2010 | Mueller et al. |
| 7,850,334 B2 | 12/2010 | Holder et al. |
| 8,002,783 B2 | 8/2011 | Vercellotti et al. |
| 8,097,865 B2 | 1/2012 | Westphal et al. |
| 8,444,629 B2 | 5/2013 | Manna et al. |
| 8,496,681 B2 | 7/2013 | Easley |
| 8,525,059 B2 | 9/2013 | Berger et al. |
| 2001/0053078 A1 | 12/2001 | Ishikawa et al. |
| 2002/0025298 A1 | 2/2002 | Blumenkranz et al. |
| 2002/0087149 A1 | 7/2002 | McCary |
| 2002/0101568 A1 | 8/2002 | Eberl et al. |
| 2003/0035301 A1 | 2/2003 | Gardiner et al. |
| 2003/0103262 A1 | 6/2003 | Descour et al. |
| 2003/0112639 A1 | 6/2003 | Stack |
| 2003/0218755 A1 | 11/2003 | Wei |
| 2004/0004846 A1 | 1/2004 | Steen et al. |
| 2004/0023415 A1 | 2/2004 | Sokolov et al. |
| 2004/0032750 A1 | 2/2004 | Watts et al. |
| 2004/0064053 A1 | 4/2004 | Chang et al. |
| 2004/0090796 A1 | 5/2004 | Steen et al. |
| 2004/0181133 A1 | 9/2004 | Al-Ali |
| 2005/0075628 A1 | 4/2005 | Cazzini et al. |
| 2005/0099824 A1 | 5/2005 | Dowling et al. |
| 2005/0128184 A1 | 6/2005 | McGreevy |
| 2005/0135095 A1 | 6/2005 | Geissler |
| 2005/0157263 A1 | 7/2005 | Sakata et al. |
| 2005/0182321 A1 | 8/2005 | Frangioni |
| 2005/0222499 A1 | 10/2005 | Banik et al. |
| 2005/0283138 A1 | 12/2005 | Tashiro et al. |
| 2006/0001842 A1 | 1/2006 | Engle |
| 2006/0120250 A1 | 6/2006 | Awamura et al. |
| 2006/0134001 A1 | 6/2006 | Frangioni |
| 2006/0152172 A9 | 7/2006 | Mueller et al. |
| 2006/0228256 A1 | 10/2006 | McDevitt et al. |
| 2006/0257941 A1 | 11/2006 | McDevitt et al. |
| 2006/0257991 A1 | 11/2006 | McDevitt et al. |
| 2006/0257992 A1 | 11/2006 | McDevitt et al. |
| 2006/0257993 A1 | 11/2006 | McDevitt et al. |
| 2006/0272979 A1 | 12/2006 | Lubbers et al. |
| 2006/0282064 A1 | 12/2006 | Shimizu et al. |
| 2007/0038121 A1 | 2/2007 | Feldman et al. |
| 2007/0115658 A1 | 5/2007 | Mueller et al. |
| 2007/0173718 A1 | 7/2007 | Richards-Kortum et al. |
| 2007/0179430 A1 | 8/2007 | Smith et al. |
| 2007/0244367 A1 | 10/2007 | Caffey et al. |
| 2008/0029708 A1 | 2/2008 | Olsen et al. |
| 2008/0038738 A1 | 2/2008 | Weigum et al. |
| 2008/0051629 A1 | 2/2008 | Sugiyama et al. |
| 2008/0095714 A1 | 4/2008 | Castella et al. |
| 2008/0167644 A1 | 7/2008 | Shelton et al. |
| 2008/0200761 A1 | 8/2008 | Schwartz et al. |
| 2008/0208000 A1 | 8/2008 | Schwartz et al. |
| 2008/0208233 A1 | 8/2008 | Barnes et al. |
| 2008/0308098 A1 | 12/2008 | Schwartz et al. |
| 2009/0009759 A1 | 1/2009 | Backman et al. |
| 2009/0016075 A1 | 1/2009 | Bhadri et al. |
| 2009/0068108 A1 | 3/2009 | Sokolov et al. |
| 2009/0146583 A1 | 6/2009 | Bhadri et al. |
| 2009/0237920 A1 | 9/2009 | Dallas et al. |
| 2010/0002428 A1 | 1/2010 | Hall et al. |
| 2010/0026957 A1 | 2/2010 | Tanguay, Jr. et al. |
| 2010/0093561 A1 | 4/2010 | Rantala et al. |
| 2010/0095969 A1 | 4/2010 | Schwartz et al. |
| 2010/0134303 A1 | 6/2010 | Perkins |
| 2010/0137687 A1 | 6/2010 | Schwartz et al. |
| 2010/0157620 A1 | 6/2010 | Bhadri et al. |
| 2010/0210951 A1 | 8/2010 | Rahman et al. |
| 2010/0262017 A1 | 10/2010 | Frangioni |
| 2010/0262020 A1 | 10/2010 | Backman et al. |
| 2010/0321772 A1 | 12/2010 | Reimer et al. |
| 2011/0112518 A1 | 5/2011 | Stanton |
| 2011/0295193 A1 | 12/2011 | Fitzgerald et al. |
| 2012/0232540 A1 | 9/2012 | Baur et al. |
| 2013/0009606 A1 | 1/2013 | Smith et al. |

FOREIGN PATENT DOCUMENTS

| | | |
|---|---|---|
| EP | 2441393 | 4/2012 |
| GB | 1349881 | 4/1974 |
| JP | 03/047249 | 2/1991 |
| JP | 2005/528733 | 9/2005 |
| JP | 2007/044245 | 2/2007 |
| WO | 92/20310 | 11/1992 |
| WO | 98/06338 | 2/1998 |
| WO | 2004/105631 | 12/2004 |
| WO | 2008/106590 | 9/2008 |
| WO | 2008/152378 | 12/2008 |
| WO | 2010/030850 | 3/2010 |

OTHER PUBLICATIONS

International Search Report and Written Opinion for PCT Application No. PCT/US2005/05521, dated Jan. 24, 2008.
International Search Report for PCT Patent Application No. PCT/US09/41723, dated Oct. 2, 2009.
International Search Report and Written Opinion for PCT Application No. PCT/US2008/55277, dated Jul. 28, 2008.
Calhoun, et al., "The Roto-Extractor in Pediatric Ophthalmology" 1975, pp. 292-305.
Douvas, "Microsurgical Roto-Extractor Instrument for Vitrectomy," New Research on the Aetiology and Surgery of Retinal Detachment, Mod. Probl. Ophtal, vol. 15, pp. 253-260, 1975.
International Preliminary Report on Patentability dated Feb. 24, 2009 for PCT Application No. PCT/US05/05521.
International Search Report and Written Opinion dated Jul. 28, 2008 for PCT Application No. PCT/US08/55277.
International Preliminary Report on Patentability dated Sep. 1, 2009 for PCT Application No. PCT/US08/55277.

* cited by examiner

FIG. 2D dr# ENHANCED VISUALIZATION ILLUMINATION SYSTEM

CROSS-REFERENCE TO RELATED APPLICATION(S)

The present application is a continuation of U.S. application Ser. No. 13/190,142, filed Jul. 25, 2011, which is a divisional of U.S. application Ser. No. 12/641,269, filed Dec. 17, 2009, now abandoned, which is a continuation of U.S. application Ser. No. 11/938,233, filed Nov. 9, 2007, now U.S. Pat. No. 7,654,716, which claims the benefit of U.S. Provisional Patent Application Ser. No. 60/858,176 filed on Nov. 10, 2006. The foregoing applications are hereby incorporated herein by reference in their entirety.

FIELD OF THE INVENTION

The present invention relates to an illumination system for surgery, and more particularly, to an illumination system for enhanced lighting conditions for ophthalmic surgery.

BACKGROUND

During surgical procedures, a surgeon depends on an operating microscope and an illuminating light source, such as, for example, an endoilluminator, to visualize the anatomical structures of the eye on which an operation is being conducted. If the surgeon experiences limited visibility in posterior eye procedures, the current protocol is to generally increase the intensity of the illuminating light source. In this regard, the medical illumination industry offers light sources with higher intensities.

The higher intensity light source, however, is not always sufficient to accurately view the fundus of the eye. The fundus is in the posterior section of the human eye, which includes the retina, blood vessels, the optic nerve, the choroid, and the like. Each of these anatomical features has a specific color when viewed with an operating microscope. During surgery, some structures can be easily seen. However other features can potentially be washed out with the bright white light of the endoilluminator.

Current attempts to overcome this problem are unsophisticated and generally involve the use of red-free light to visualize certain features of the fundus such as the retinal blood vessels and pathologic focal atrophy of the nerve fiber layer. Accordingly, what is desired is an illumination system that improves the quality, intensity, and contrast of light to provide surgeons with better illumination during ophthalmic surgery.

SUMMARY OF THE INVENTION

An aspect of an embodiment of the present invention is directed toward an enhanced illumination system that improves the quality, intensity, and contrast of light.

An embodiment of the present invention provides an enhanced illumination system including: a light source configured to produce a light beam; an angling device configured to receive light produced by the light source and configured to be adjusted to a first position for reflecting at least a portion of the light beam in a first angled direction, and further configured to be adjusted to a second position for allowing the light beam to bypass the angling device; a mirror configured to reflect at least a portion of the light beam in response to the angling device being adjusted to the first position; a first output port for outputting the at least a portion of the light beam reflected by the mirror; and a second output port for outputting the light beam bypassing the angling device in response to the angling device being adjusted to the second position.

The enhanced illumination system may further include a light filter configured to receive the first light beam and generate a filtered light beam for transmitting to the first angling device.

The enhanced illumination system may further include a coupling system configured to couple the portion of the light beam to an optical fiber coupled to the first output port.

The enhanced illumination system may further include a shutter configured to receive the light beam from the light source and adjust an intensity of the light beam.

The mirror may be a substantially curved mirror.

The angling device may include a mirror or a beam splitter.

Another embodiment of the present invention provides an enhanced illumination system including: a first light source configured to produce a first light beam with a first intensity; a second light source configured to produce a second light beam with a second intensity; at least one light filter device configured to receive the first light beam and transmit a filtered portion of the first light beam; a first angling device configured to be adjusted to a first position for reflecting the filtered portion of the first light beam in a first angled direction; a second angling device configured to be adjusted to a second position for reflecting at least a portion of the second light beam in a second angled direction; a mirror configured to receive and reflect at least the filtered portion of the first light beam reflected by the first angling device and at least a portion of the second light beam for forming a converged light beam with a third intensity; and an output port for outputting the converged light beam.

The light filter device may be configured to filter out light of particular bandwidths.

The enhanced illumination may further include a coupling system configured to couple the converged light beam to an optical fiber coupled to the output port.

The enhanced illumination may further include a first shutter configured to adjust the first intensity of the first light source and a second shutter configured to adjust the second intensity of the second light source.

The mirror may be a substantially curved mirror.

The angling device may be a mirror or a beam splitter.

The converged light beam may converge bandwidth limited light from the first light source with substantially white light from the second light source.

The third intensity of the converged light beam may be greater than the first or second intensity alone.

Another embodiment of the present invention provides a method for generating enhanced illumination that includes: producing by a first light source a first light beam with a first intensity; producing by a second light source a second light beam with a second intensity; receiving the first light beam by a light filter device and transmitting a filtered portion of the first light beam; reflecting by a first angling device the filtered portion of the first light beam in a first angled direction; reflecting by a second angling device at least a portion of the second light beam in a second angled direction; receiving and reflecting by a mirror to reflect at least the filtered portion of the first light beam reflected by the first angling device and at least the portion of the second light beam reflected by the second angling device for forming a converged light beam with a third intensity; and outputting the converged light beam at an output port.

The method may further include configuring a first lens system to couple the first light beam to a first optical fiber, configuring a second lens system to couple the second light beam to a second optical fiber, and configuring a third lens system to couple the converged light beam to a third optical fiber.

The method may further include configuring a first shutter to adjust the first intensity of the first light source and configuring a second shutter to adjust the second intensity of the second light source.

The mirror may be a substantially curved mirror.

The angling device may be a mirror or a beam splitter.

DETAILED DESCRIPTION

Surgeons generally need high intensity light to perform different types of eye surgeries, including vitreo retinal procedures. In a vitreo retinal procedure, the vitreous is removed by using small instrumentation through small openings (e.g. sclerotomies) in the wall of the eye. This procedure is commonly referred to as a pars plana vitrectomy. However, illumination through small sclerotomies inside the dark cavity of the eyeball is a challenge. In some cases, opacities inside the eye further degrade visualization. In addition, certain anatomical features of the fundus are not visible with the white light emitted via the illumination source.

According to one embodiment, bandwidth limited light may be used to enhance visualization of the fundus. For example, red-free light may be used for enhancing fundus photography and examination of the nerve fiber layer. Bandwidth limited light may also improve the contrast of fundus details and reduce (or eliminate) the loss of image quality associated with chromatic aberrations. Furthermore, the visualization and documentation of fundus structures may be improved and details may be distinguished which would otherwise be invisible with white light. The use of bandwidth limited light therefore improves the ability to differentiate fundus details by observing changes in their appearance under different bandwidths. Further, structures may be more accurately localized with regard to depth in the stratified layers of the fundus.

Accordingly, various embodiments of the present invention are directed to an enhanced illumination system that combines two or more light sources to provide different light quality, intensities, contrasts, and/or colors. Thus, depending on the particular need during surgery, the surgeon may manipulate the enhanced illumination system to combine the output of the two or more light sources into a single output that provides light that is enhanced or otherwise different over what would be output with only one of the light sources. The surgeon may also manipulate the enhanced illumination system to invoke only one of the light sources to provide white light or bandwidth limited light. Thus, the various lighting needs of the surgeon during different parts of the surgery may be met via the single enhanced illumination system.

Figure 1:
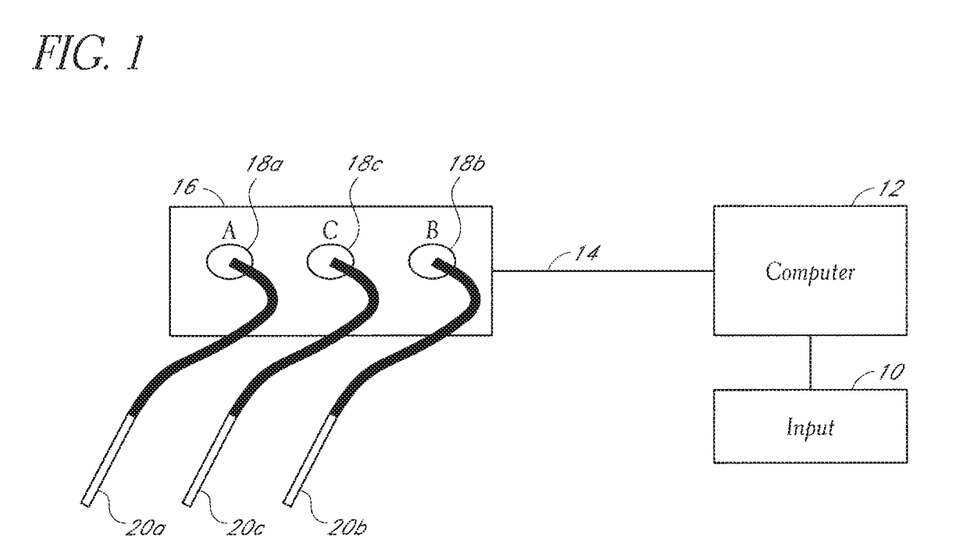
FIG. 1 is a schematic block diagram of an enhanced illumination control system according to one embodiment of the invention.

FIG. 1 is a schematic block diagram of an enhanced illumination control system according to one embodiment of the invention. The system includes an illumination system 16 coupled to a computer 12 over a data communications link 14. The communications link 14 may be a direct wire, an infrared data port, a wireless communications link, local area network link, or any other communications medium known in the art.

According to one embodiment of the invention, the illumination system includes various output ports (or channels) 18a, 18b, 18c configured to be coupled to one of more illumination outputs 20a, 20b, 20c such as, for example, a fiber optic cable or light pipe. According to one exemplary embodiment, output port A is configured to output white light of a specified intensity, output port B is configured to output light of limited bandwidth, and output port C is configured to output light that is a combination of the light that would be output at port A and that would be output at port B. As a result, the light output at port C may be a light that has an intensity greater than what is output at port A or port B alone. In addition, the light that is output at port C may be light that is tinted as a result of the combination of the white light output at port A and the bandwidth limited light output at port B. Of course, a person of skill in the art should understand that port A may be configured so that in addition or in lieu of the white light that is output by port A, port A may also be configured to output bandwidth limited light. In addition, port B may be configured so that in addition or in lieu of the bandwidth limited light that is output by port B, port B may also be configured to output white light.

According to one embodiment of the invention, the computer 12 is configured with a memory containing computer program instructions that are executed by a processor for configuring and controlling the illumination system 16. The computer program instructions may provide, for example, a graphical user interface (GUI) which allows the user to view, set, and modify different parameters for controlling the light that is output via the output ports 18a, 18b, 18c. A user input device 10 coupled to the computer 12, such as, for example, a keypad, keyboard, stylus, and the like, facilitates user control of the different parameters. The computer may also provide a screen that incorporates pressure-sensitive (touch screen) technology so that a user may view, set, and modify the different parameters by merely touching certain portions of the screen.

For example, the GUI may provide a turn on/off parameter for port A, turn on/off parameter for port B, light intensity parameter for port A, light intensity parameter for port B, filter selection parameter for port A, filter selection parameter for port B, and/or select/deselect parameter for port C. Each of these parameters may be set by a doctor or nurse prior to or during a particular ophthalmic procedure. According to one embodiment of the invention, computer program instructions are provided to process the entered parameters and transmit appropriate commands to the enhanced illumination system 16 for causing a desired type of illumination to be output via the selected port.

According to one embodiment of the invention, one or more mechanical buttons or switches may be provided by the illumination system 16 for being directly manipulated by a user in order to configure and set the various lighting parameters.

Figure 2A:
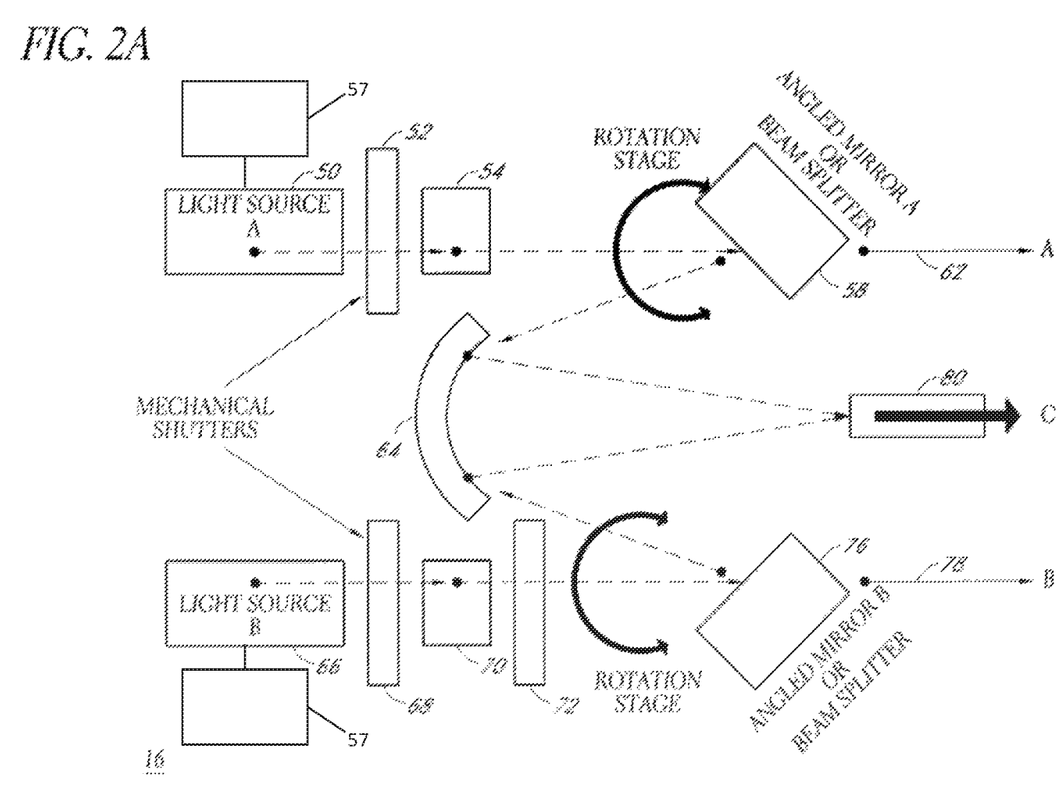
FIG. 2A is a more detailed schematic diagram of an enhanced illumination system in the enhanced illumination control system of FIG. 1 according to one embodiment of the invention.

FIG. 2A is a more detailed schematic diagram of the enhanced illumination system 16 according to one embodiment of the invention. In the embodiment illustrated in FIG. 2A, the enhanced illumination system includes a light source A 50 and a light source B 66 which respectively emit light beam A and light beam B. Light beam A and light beam B are converged downstream into light beam C and output via output port C 18c. According to one embodiment, converged light beam C has an intensity greater than the intensity of light beam A or light beam B alone.

More specifically, light source A 50 may emit light beam A through a mechanical shutter 52 that has an opening area that may be increased or decreased to respectively increase or decrease light intensity based on monitoring of the light path via a feedback system (not shown), and/or one or more commands from the computer 12. A person of skill in the art should understand that the mechanical shutter 52 may take any form conventional in the art. Light source A may be a halogen lamp, metal halide lamp, xenon, lamp, em-arc lamp, LED, or any other light source conventional in the art.

The light emitted from light source A is focused and collimated via a lens system 54. According to one embodiment of the invention, the lens system 54 is formed via one or more concave, convex, and/or meniscus lens, which allow increased coupling of the light beam A.

According to one embodiment of the invention, the collimated light beam A is received and reflected by an angling device 58. The angling device 58 may take the form of a mirror, beam splitter, or any like device conventional in the art that is capable of being rotated into a particular angle to allow light to be reflected onto one or more mirrors 64. According to one embodiment of the invention the light reflected by the angling device 58 is received by a single curved mirror and is in turn reflected by the mirror onto a coupling system 80. According to another embodiment of the invention, two flat mirrors placed at an angle may replace the single curved mirror.

The coupling system 80 focuses and collimates light beam A into output port C 18c. Output port C may be, for example, an optical fiber channel.

The coupling system 80 also focuses and collimates light beam B from light source B 66. Light source B may be of a type similar to light source A. In this regard, light source B emits light through a mechanical shutter 68 which may be similar to the mechanical shutter 52 for light source A. The light emitted from the light source 66 is focused and collimated via a lens system 70 which may be similar to the lens system 54 for light source A.

According to one embodiment of the invention, at least one light filter device 72, such as a filter or a filter wheel including multiple filters, is placed in the path of collimated light beam B. According to one embodiment of the invention, the filter device 72 is adjusted based on one or more commands from the computer 12 to allow all or only certain bandwidths of the collimated light beam B to pass through. For example, the filter device 72 may block red light and allow other colors of light beam B to pass to generate a substantially red-free light. The filter device 72 may also be adjusted to allow or block other colors of light. The generating of a bandwidth dependent wavelength helps improve the viewing of the different structures of the fundus of the eye. The light filtering device 72 may also act as an attenuator to control light intensity.

According to one embodiment of the invention, light passing through the light filter device 72 is received and reflected by an angling device 76 which may be similar to the angling device 58 for light source A. The angling device 76 is rotated to a particular position for allowing the light beam to be reflected onto the mirror 64 and onto the coupling system 80. In this manner, light beam A and light beam B are combined in output port C 18C to generate a light beam C which has a greater intensity than light beam A or light beam B alone. In addition, the combination of light beam A in the form of a white light and light beam B in the form of a limited bandwidth light results in light beam C which is referred to a tinted light. Tinted light is beneficial because it enhances the contrast of fundus details.

In another embodiment of the invention, the coupling system 80 is replaced with a 2×1 optical coupler that combines light beam A and light beam B to light beam C.

Although the enhanced illumination system described with respect to FIG. 2A includes angling devices 58, 76 for both light source A 50 and light source B 66, a person of skill in the art should recognize that only one of the light sources may be Coupled to the angling device.

Figure 2B:
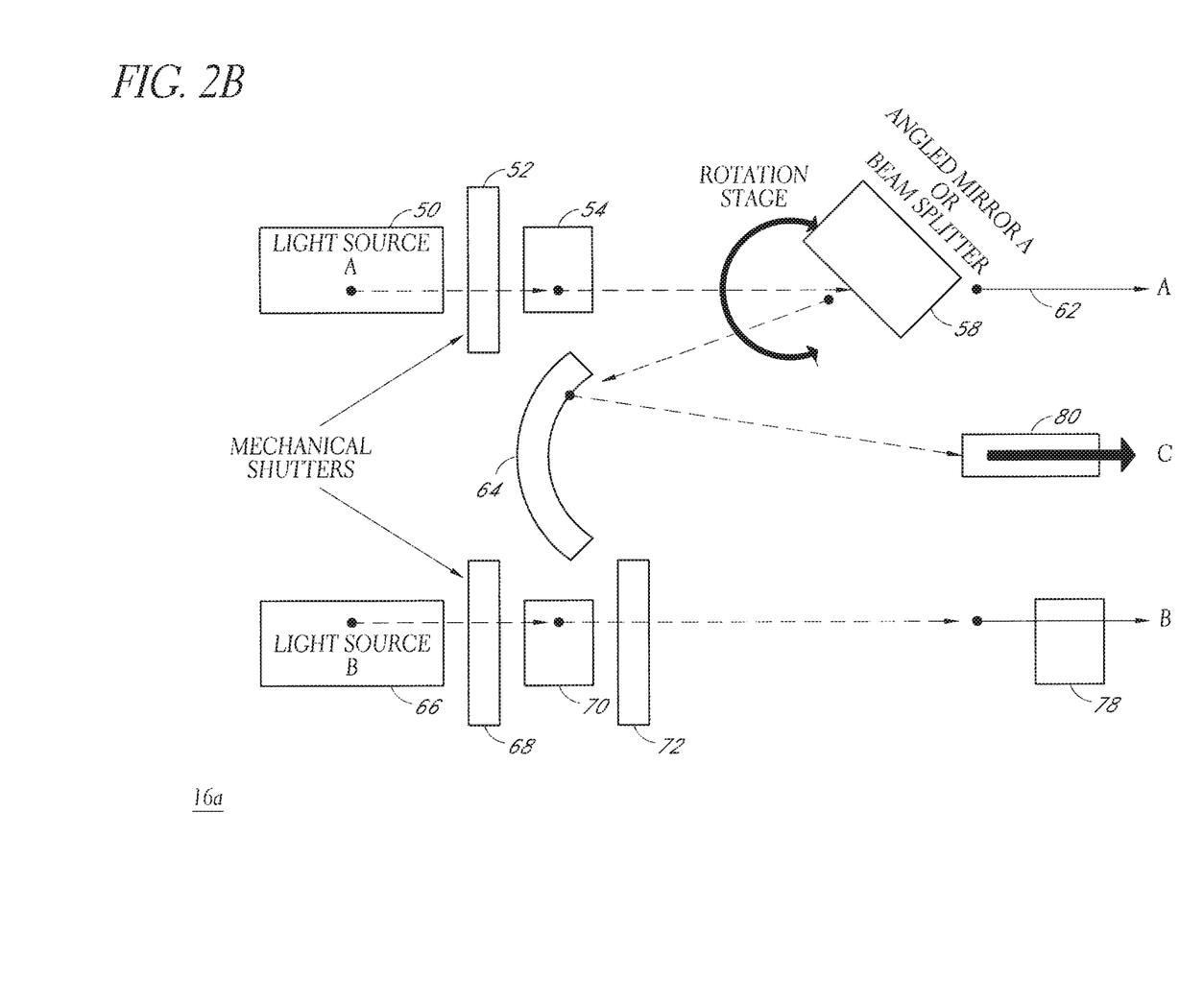
FIG. 2B is a schematic diagram of an enhanced illumination system according to an alternative embodiment of the invention with one light source coupled to an angling device.

FIG. 2B is a schematic diagram of an enhanced illumination system 16a according to an alternative embodiment of the invention where only one of the light sources is coupled to an angling device. In the embodiment illustrated in FIG. 2B, only light source A is coupled to the angling device 58, causing light beam A to reflect onto the mirror 64 for being output via output port C as light beam C. Light source B is not coupled to the angling device. Thus, light beam B is focused and collimated by a coupling system 78 which may be similar to the coupling system 80 for output via output port B.

Alternatively, instead of eliminating one or more angling devices, the one or more of the angling devices may be configured to be rotated into a first position when convergence of light beams is desired, and rotated into a second bypass position when convergence is not desired.

Figure 2C:
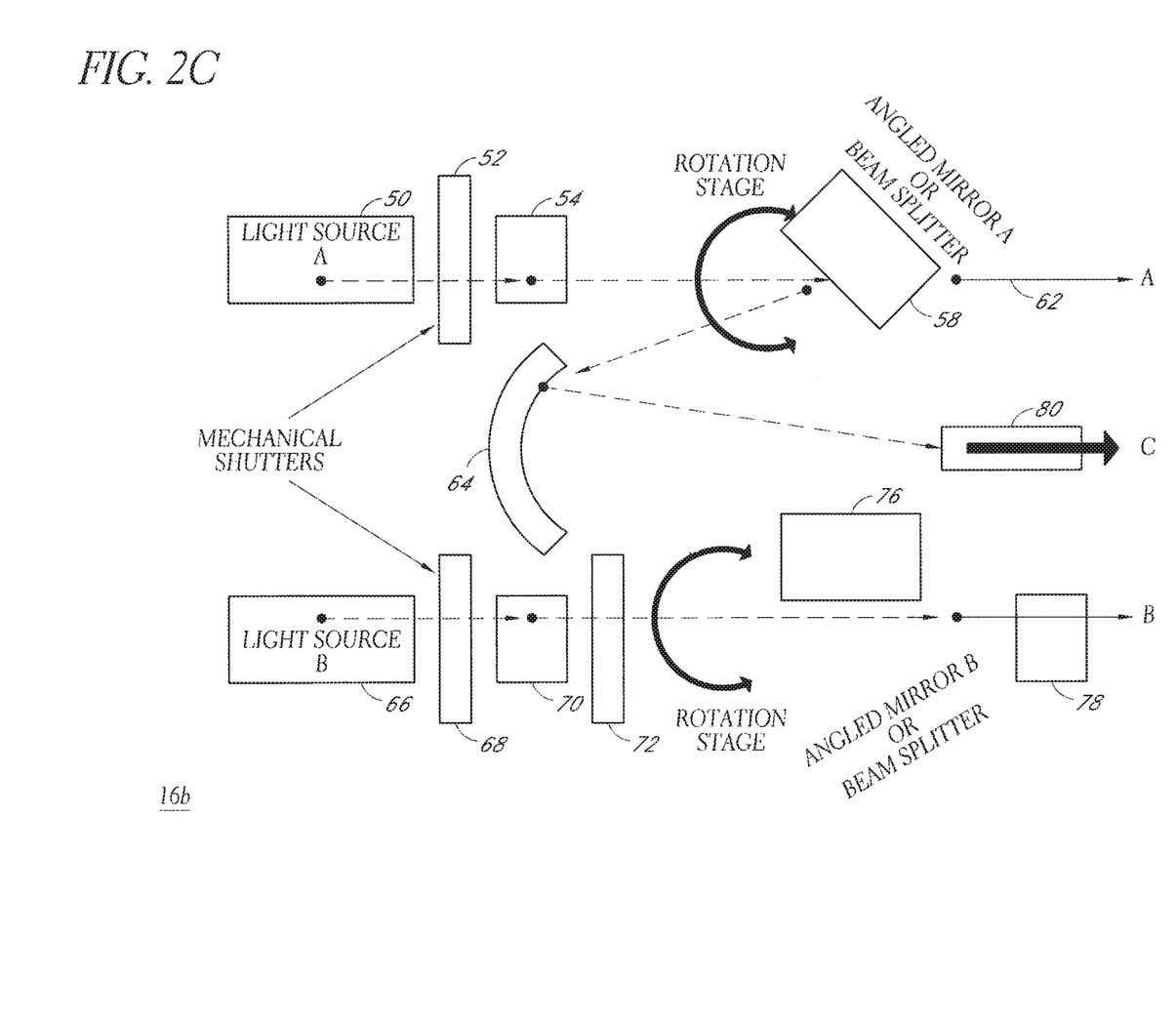
FIG. 2C is a schematic block diagram of an enhanced illumination system with an angling device positioned in the bypass position.

FIG. 2C is a schematic block diagram of an enhanced illumination system 16b with one of the angling devices positioned in the bypass position. According to this embodiment, the angling device 76 associated with light source B is placed in the bypass position in response to one or more commands from the computer 12. When placed in the bypass position, the angling device 76 is not in the path of light beam B. As a result, light beam B is received by the coupling system 78 which focuses and collimates the light into the output port B.

Figure 2D:
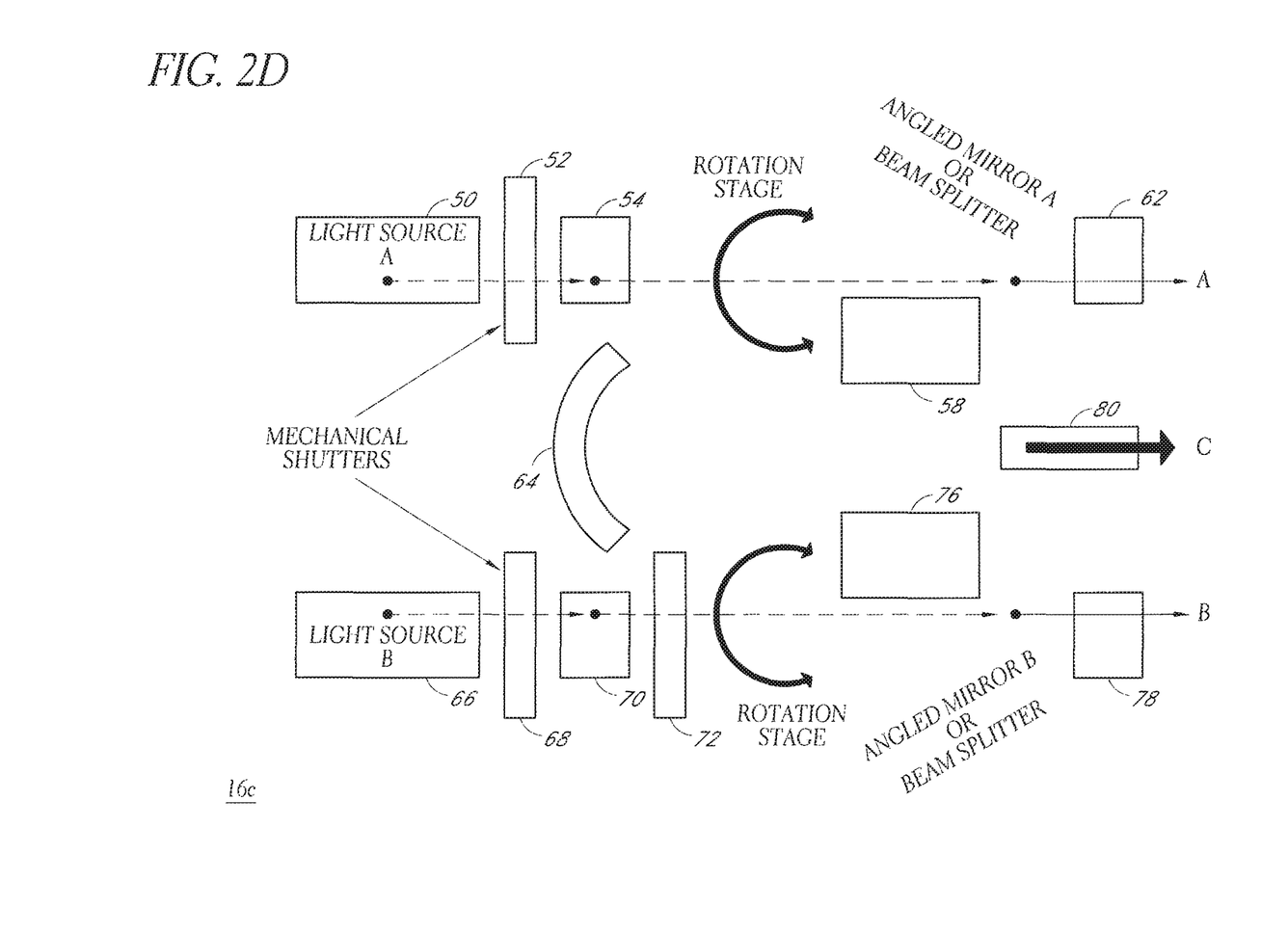
FIG. 2D is a schematic block diagram of an enhanced illumination system with two angling devices positioned in a bypass position.

FIG. 2D is a schematic block diagram of an enhanced illumination system 16c with both of the angling devices positioned in the bypass position. According to this embodiment, both the angling device 58 and the angling device 76 are placed in the bypass position. In this regard, neither the angling device 58 nor the angling device 76 is in the path of light beam A or light beam B. As a result, light beam A is received by a coupling system 62 which focuses and collimates the light into the output port A, and light beam B is received by the coupling system 78 which focuses and collimates the light into the output port B.

Figure 3:
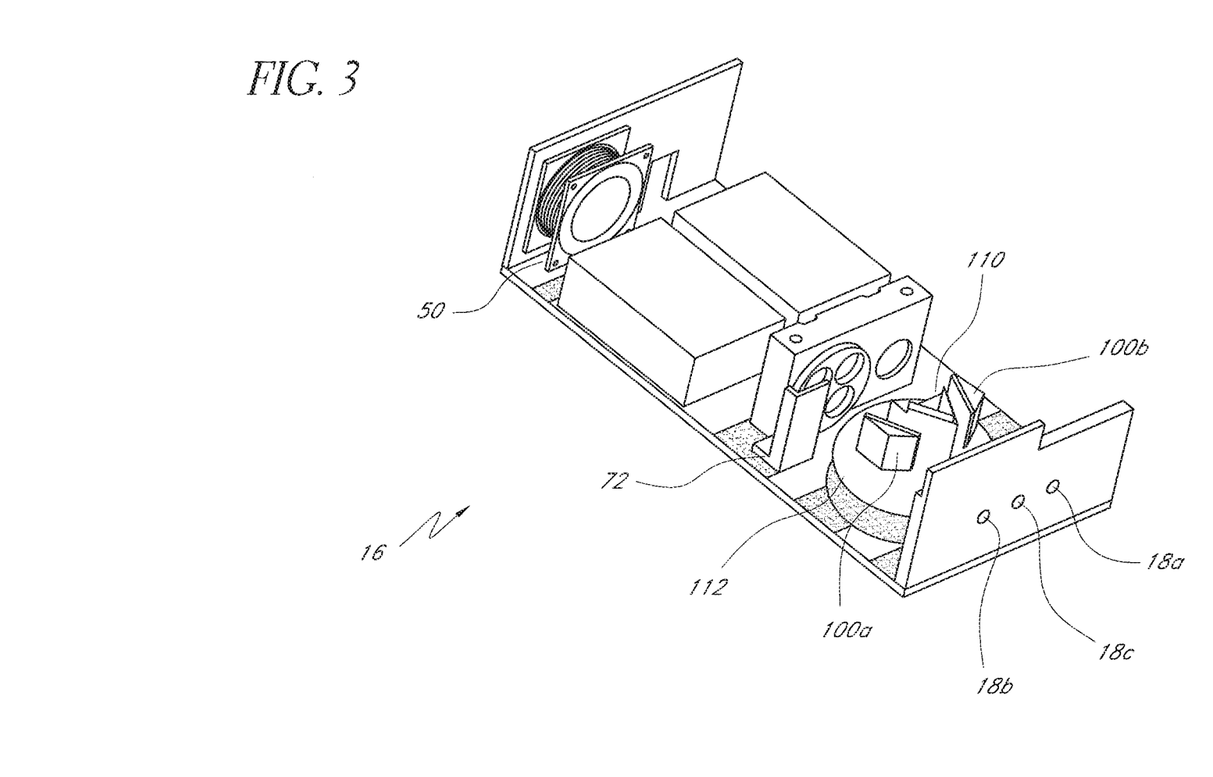
FIG. 3 is a photographic image of an enhanced illumination system according to another embodiment of the invention.

FIG. 3 is a photographic image of an enhanced illumination system 16c according to another embodiment of the invention. According to this embodiment, a mirror 110 and angling devices 100*a* and 100*b* are mounted on a rotation device 112. In this regard, the angling devices 100*a* and 100*b* are rotated to a particular position for allowing the light beams A and B to be reflected onto the mirror 110 and combine in output port C 18C to generate a light beam C. Alternatively, the rotation device 112 may be rotated so that the mirror 110 and angling devices 100*a* and 100*b* are placed in a bypass position. In this regard, neither the angling device 100*a* or angling device 100*b* is in the path of light beam A or light beam B. As a result, light beam A is output via output port A 18*a* and light beam B is output via output port B 18*b*. A fan 50 may also be included to cool the enhanced illumination system 16.

In another embodiment of the invention a sensor system 57 coupled to one or more of the light sources may be used to monitor the bulb functionality and spectrum stability of the one or more light sources.

According to one embodiment of the invention, the enhanced illumination system is integrated into a vitrectomy machine. The integration into the vitrectomy machine provides practical advantages from an economic, transportability, ergonomic, and usability standpoint. Furthermore, the enhanced illumination system is designed to give the surgeon the option of using a single light source to cause light to be output by either output port A or output port B, or a combination of two light sources for complimentary illumination via output port C. For example, during a portion of a surgery that requires only white light of a desired intensity, the surgeon may cause the computer 14 to transmit commands to the illumination system to actuate port A for outputting white light with the desired intensity. In this regard, the angling device 58 may be rotated to be in a bypass mode, and ports B and C may be disabled. If however, instead of white light, bandwidth limited light is desired, the surgeon may alter the settings of the computer to cause the computer to transmit commands to the illumination system to actuate port B for outputting limited bandwidth light. In addition, if during a different portion of the surgery tinted light is desired for better visibility of the internal structures of the fundus, the surgeon may alter the settings of the computer to cause the computer to transmit commands to rotate the angling devices 58, 76 to be in angled positions to cause convergence of the white light from light source A and the bandwidth limited light from light source B, and actuate port C to cause output of the converged light via port C that is tinted for better contrast and has a higher intensity than the intensity allowed by light source A or B alone. Of course, a person of skill in the art should recognize that white light of higher intensity may also be provided by disabling the filter device coupled to light source B, and causing the convergence of white lights from light source A and light source B.

A person of skill in the art should recognize that the claimed enhanced illumination system allows for a high optical output intensity, in addition to improved visualization. For example, the use of bandwidth limited wavelength light allows physicians to operate with improved contrast for visualization of specific structures in the eye. Additional features include controlling not only the intensity, but also the quality of the light, which is improved by changing the color (or color temperature) of the light from the light source via the filter device 72, with the light produced from one or more channels.

The illumination system allows for various novel applications, including use inside the operating room or outside the operating room (office based procedures) for not only ophthalmic procedures but any other procedure that mayor may not relate to a human body by providing a high intensity output. The illumination system also allows for improved structural viewing by color contrasts, one or more outputs (with variable intensity and color), compatibility with numerous light sources (such as halogen, metal halide, xenon and em-arc), and/or constant monitoring of the status of the light source.

Furthermore, to those skilled in the various arts, the invention itself herein will suggest other variations to the described embodiment which in no way depart from the scope and spirit of the present invention. For example, although a filter wheel is depicted as being coupled to only light source B, a person of skill in the art should recognize that the filter wheel may also be coupled to light source A. Furthermore, a single light source or more than two light sources may be used in alternative embodiments of the enhanced illumination system in providing light beams A and B. In another embodiment, the enhanced illumination system may be implemented without the lens system. Furthermore, a person of skill in the art should also recognize that the various components of the enhanced illumination system of the above embodiments may be implemented as separate physical components, or one or more of the functionalities of the various components combined into a single physical component or housed in a single physical housing.

Furthermore, to those skilled in the various arts, the invention itself herein will suggest solutions to other tasks and adaptations for other applications. It is the Applicants' intention to cover all such uses of the invention and those changes and modifications which could be made to the embodiments of the invention herein chosen for the purpose of disclosure without departing from the spirit and scope of the invention. Thus, the present embodiments of the invention should be considered in all respects as illustrative and not restrictive.

What is claimed is:

1. A method for generating enhanced illumination, the method comprising:
   producing by a first light source a first light beam with a first intensity;
   coupling the first light beam to a first optical fiber;
   producing by a second light source a second light beam with a second intensity;
   coupling the second light beam to a second optical fiber;
   receiving the first light beam by a light filter device and transmitting a filtered portion of the first light beam;
   reflecting by a first angling device the filtered portion of the first light beam in a first angled direction;
   reflecting by a second angling device at least a portion of the second light beam in a second angled direction;
   receiving and reflecting by a mirror at least the filtered portion of the first light beam reflected by the first angling device and at least the portion of the second light beam reflected by the second angling device for forming a converged light beam with a third intensity;
   outputting the converged light beam at an output port; and
   coupling the output port to a third optical fiber.

2. The method of claim 1, further comprising configuring a first shutter to adjust the first intensity of the first light source and configuring a second shutter to adjust the second intensity of the second light source.

3. The method of claim 1, wherein the mirror is a substantially curved mirror.

4. The method of claim 1, wherein at least one of the first or second angling device comprises a mirror.

5. The method of claim 1, wherein at least one of the first or second angling device comprises a beam splitter.

6. The method of claim 1, wherein the light filter device is configured to filter out light of particular bandwidths.

7. The method of claim 1, wherein the converged light beam converges bandwidth limited light from the first light source with substantially white light from the second light source.

8. The method of claim 1, wherein the third intensity of the converged light beam is greater than the first or second intensity alone.

9. The method of claim 1, wherein the converged light beam comprises red-free light for nerve fiber layer examination.

10. The method of claim 1, wherein converged light beam comprises bandwidth limited light to reduce chromatic aberrations.

* * * * *